United States Patent [19]

Mathai

[11] Patent Number: 5,004,828

[45] Date of Patent: Apr. 2, 1991

[54] HYDROXY-FUNCTIONAL POLYESTER DILUENTS AS ADDITIVES IN COATING COMPOSITIONS

[75] Inventor: John Mathai, Chicago, Ill.

[73] Assignee: The Sherwin-Williams Company, Cleveland, Ohio

[21] Appl. No.: 43,051

[22] Filed: Apr. 27, 1987

[51] Int. Cl.$^5$ .............................................. C07C 69/52
[52] U.S. Cl. .................................... 560/224; 560/205
[58] Field of Search ................. 524/311; 560/204, 205

[56] References Cited

U.S. PATENT DOCUMENTS

| | | | |
|---|---|---|---|
| 4,243,705 | 1/1981 | Yapp et al. | 427/836 |
| 4,451,600 | 5/1984 | Fry | 524/196 |
| 4,560,494 | 12/1985 | Druetzler | 252/182 |
| 4,619,955 | 10/1986 | Druetzler | 524/29 |

Primary Examiner—Joseph L. Schofer
Assistant Examiner—J. M. Reddick
Attorney, Agent, or Firm—Robert E. McDonald; Steven W. Tan

[57] ABSTRACT

This invention relates to novel hydroxy-functional polyester diluents, and more particularly, to acrylic-modified hydroxy-functional polyester reactive diluents useful for blending with a variety of thermosetting or thermoplastic film-forming polymers. More specifically, the hydroxy-functional polyester reactive diluents are essentially low molecular weight polyesters derived from triols, and a combination of unsaturated monocarboxylic acids and saturated monocarboxylic acids. These hydroxy-functional polyester diluents may be compolymerized with one or more acrylic monomers, i.e. hydroxy-functional acrylic monomers, and blended with a variety of thermosetting or thermoplastic film-forming polymers. These blends of the film-forming polymers and the hydroxy-functional polyester diluents can be crosslinked with conventional crosslinking agents as isocyanates and used in the formulation of low VOC paint compositions particularly useful as automotive topcoats.

2 Claims, No Drawings

HYDROXY-FUNCTIONAL POLYESTER DILUENTS AS ADDITIVES IN COATING COMPOSITIONS

BACKGROUND OF THE INVENTION

This invention is directed to a novel hydroxy-functional polyester and more specifically to an acrylic-modified hydroxy-functional polyester useful as a diluent with a wide variety of thermoplastic or thermosetting paint vehicles. More specifically, this invention is directed to hydroxy-functional polyester diluents and acrylic-modified hydroxy-functional polyester diluents useful with a wide variety of thermoplastic or thermosetting polymeric film-forming polymers.

The thermoplastic and thermosetting film-forming vehicles or polymers such as the polyurethanes, alkyds, acrylics, and polyesters are well-known as vehicles for coating compositions and have been applied on a variety of substrates. The formulation of these vehicles in coatings can be varied to optimize the desired performance characteristics. However, in some instances optimizing one characteristic can adversely effect the other desirable characteristics required of a particular coating. For example, in refinishing automobile or truck bodies a variety of thermoplastic and thermosetting film-forming polymers are used and include such polymeric vehicles as the acrylic lacquers and enamels, the nitrocellulose lacquers, the alkyd enamels, the polyester enamels, the polyurethane enamels and the like. These vehicles must have sufficient flexibility for application to various substrates, i.e. metal parts, but may not be sufficient for the more flexible plastic materials utilized in today's automobile and truck bodies.

The hydroxy-functional polyester diluents, including the acrylic-modified polyester diluents of this invention have excellent compatibility with a wide variety of film-forming polymers and are particularly adaptable for use as automotive topcoats. Upon curing, these coatings form a glossy durable finish, exhibit excellent adhesion to metal with superior pigment dispersibility and are resistance to solvents. The preferred coating can be formulated to contain more than about 75%, e.g. up to about 90%, by weight of non-volatile solids. Because of the strict solvent emission regulations of recent years, low solvent emission coatings have become very desirable and a number of low VOC paint compositions have been proposed to meet these requirements. However, many of the available coatings are deficient in this regard because of the difficulty in application, adhesion, lack of flexibility, poor durability, poor pigment dispersibility and low solvent resistance. Therefore, many of these coatings are deficient for use as automotive topcoats, especially when the topcoat includes a metallic flake as the pigment. The low viscosity of these coatings are not sufficient to immobilize the flakes which tend to redistribute and thereby give a nonuniform distribution in the film. The coatings of this invention, however, combine the desired characteristics, e.g. good pigment dispersibility, etc., with the low application viscosity and are therefore particularly adaptable for automotive and truck body topcoats including coatings which use metallic flakes as the pigment.

The prior art required the use of mixtures of polyisocyanates with polyesters such as disclosed in U.S. Pat. No. 4,451,600 and U.S. Pat. No. 4,419,293. These additives, however, are not adequate for preparing coatings comprising polymeric low volatile organic compound (VOC) compositions adapted for use as automotive topcoats. Moreover, the coating compositions of this invention are capable of being cured at ambient temperatures, i.e. low bake and can be used in combination with a variety of pigments, including metallic flakes. Thus, the coating compositions of this invention have more than about 75% by weight of nonvolatile solids exclusive of the pigment and other nonreactive components and comprise a low molecular weight polyester with pendent hydroxy functional groups and polymerizable double bonds and have a number average weight ranging up to about 500 and more likely in the range of 140 to 300.

SUMMARY OF THE INVENTION

This invention relates to hydroxy-functional polyester diluents and more specifically to acrylic-modified hydroxy-functional polyester diluents capable of being blended with a wide variety of conventional vehicles, e.g. acrylics, alkyds, acrylic-modified alkyds, polyesters and the like. The coating compositions of this invention comprise up to about 75 parts by weight, i.e. from 1 to 75 parts by weight, of the hydroxy-functional reactive diluent or its acrylic-modified polymer and from about 25 to 99 parts by weight of a conventional film forming thermoplastic or thermosetting resin and from 0 to 30 parts by weight of a crosslinking agent which results in less than a 3.0–3.5 VOC coating curable at ambient or room temperatures, i.e. low bake temperatures. The hydroxy-functional polyester diluent and the acrylic-modified copolymers thereof have a number average molecular weight of between 100 and 500 and preferably between 140 and 300 and comprise at least one hydroxy functionality, e.g. 1 to 2 hydroxyl groups, and at least one reactive double bond within the molecule. The reactive polyester diluents are derived from at least one polyol, i.e. a triol, at least one low molecular weight unsaturated monocarboxylic acid and at least one low molecular weight saturated monocarboxylic acid. The hydroxy-functional polyester reactive diluents may, if desired, be further modified with at least one acrylic monomer, e.g. a hydroxy-functional acrylic monomer, to form the copolymer. The copolymer is obtained from 0 to 50 parts by weight of the acrylic monomer and 50 to 100 parts by weight of the hydroxy-functional polyester or the acrylic-modified hydroxy-functional polyester diluent.

Accordingly, it is an object of this invention to provide a novel hydroxy-functional polyester diluent compatible with a variety of paint vehicles. It is another object of this invention to provide an acrylic-modified hydroxy-functional polyester diluent compatible with a variety of conventional polymeric film-forming paint vehicles. It is another object of this invention to provide a hydroxy-functional polyester reactive diluent and the acrylic-modified hydroxy-functional polyester diluents which can be crosslinked with a conventional crosslinking agent. It is a further object of this invention to provide hydroxy-functional polyester reactive diluents capable of being blended with a variety of film-forming paint vehicles to form coatings which cure at ambient or room temperature characterized as having less than 3.0 to 3.5 VOC. It is a further object of this invention to provide unique coating compositions particularly useful for automotive bodies comprising hydroxy-functional polyester reactive diluents and the acrylic-modified hydroxy-functional polyester reactive diluents for use in combination with a variety of thermosetting or thermoplastic film-forming vehicles.

These and other objects of the invention will become apparent from the following description.

DETAILED DESCRIPTION OF THE INVENTION

More specifically, this invention relates to hydroxy-functional polyester reactive diluents having a number average molecular weight less than about 500 and preferably from about 140 to 300 characterized as having at least one hydroxy group, e.g. from 1 to 2 hydroxy groups, per molecule with an average of at least one polymerizable double bond per molecule. The hydroxy-functional polyesters are derived from at least one polyol, i.e. a triol, and at least one low molecular weight unsaturated monocarboxylic acid and at least one low molecular weight saturated monocarboxylic acid. The polyol, i.e. triol, is present in a stoichiometric amount to provide an excess number of hydroxyl groups with the unsaturated monocarboxylic acid being present in an amount sufficient to provide at least one ethylenically unsaturated group for each molecule of polyol. More specifically, the hydroxy-functional polyester diluents of this invention are derived from the reaction of about 40 to 60 parts by weight of at least one triol, 10 to 30 parts by weight of a low molecular weight unsaturated monocarboxylic acid, 10 to 30 parts by weight of a low molecular weight saturated monocarboxylic acid and 0 to 15 parts by weight of a benzoic acid, i.e. tertiary butyl benzoic acid. The hydroxy-functional polyester diluents can be further modified with an acrylic monomer by reacting, for example, 50 to 100 parts by weight of the hydroxy-functional polyester diluent having a number average molecular weight less than about 500 with about 0 to 50 parts by weight, e.g. 10 to 30 parts, of at least one acrylic monomer capable of copolymerizing with the hydroxy-functional polyester reactive diluent.

These hydroxy-functional polyester diluents and the acrylic-modified hydroxy-functional polyester diluents may be blended with conventional thermosetting or thermoplastic film-forming polymers. More specifically, coating compositions may be prepared with a hydroxy-functional polyester diluent having a number average molecular weight less than about 500 derived from the reaction of from about 40 to 60 parts by weight of at least one triol, 10 to 30 parts by weight of the unsaturated monocarboxylic acid, 10 to 30 parts by weight of the saturated monocarboxylic and 0 to 15 parts by weight of a benzoic acid. The hydroxy-functional polyester diluents or the acrylic-modified hydroxy-functional polyester diluents can be blended with 25 to 99 parts by weight of a conventional film-forming paint vehicle such as acrylic polymers, alkyd polymers, polyesters and the like. Specifically, coating compositions can be prepared by blending approximately 1 to 75 parts by weight of the hydroxy-functional polyester diluent or preferably 10 to 50 parts by weight of the hydroxy-functional polyester diluent or in the alternative the acrylic-modified hydroxy-functional polyester diluent with approximately 25 to 99 parts by weight and preferably 50 to 90 parts by weight of a conventional thermosetting or thermoplastic film-forming vehicle. Blends of the hydroxy-functional polyester diluent or the acrylic-modified hydroxy-functional polyester diluent blended with either a thermosetting or thermoplastic film-forming polymer may contain up to 40 parts by weight of pigment such as titanium dioxide and various other conventional additives generally incorporated into paints.

The hydroxy-functional polyester diluents of this invention are prepared by reacting the triol, such as trimethylolpropane, with the unsaturated monocarboxylic acid, e.g. crotonic acid, and the saturated monocarboxylic acid, e.g. propionic acid, in a solvent such as xylene. The reactants are heated to temperatures ranging up to about 450° F. until a product is obtained which is characterized as having a number average molecular weight (Mn) ranging from about 100 to 500 and has at least one hydroxy-functional group and at least one reactive double bond within the molecule. These hydroxy-functional polyester reactive diluents can be further modified by reacting one or more acrylic monomers such as the hydroxy-substituted acrylic monomers with the polyester diluent at temperatures ranging up to about 325° F. The acrylic monomer may be used to modify the hydroxy-functional polyester diluents in amounts ranging up to about 50 parts by weight, e.g. 1 to 30 parts, of the acrylic monomer based on the total amount of the reactive polyester diluent.

The polyols, i.e. the triols, preferably have molecular weight of less than about 200 and include such low molecular weight compounds as trimethylolethane, trimethylolpropane, glycerol and the like.

The low molecular weight unsaturated monocarboxylic acids are used in amounts ranging from about 10 to 30 parts by weight and preferably in amounts ranging from about 15 to 25 parts by weight. More specifically, the unsaturated monocarboxylic acids, such as crotonic acid, may be characterized by the formula:

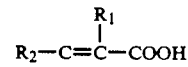

wherein $R_1$ is either hydrogen or an alkyl group of 1 to 3 carbon atoms and $R_2$ is an aliphatic group of 1 to 4 carbon atoms or an aryl group. The preferred unsaturated monocarboxylic acids include crotonic acid, tiglic acid, cinnamic acid, and various mixtures of any of these acids in any proportion.

The low molecular weight saturated monocarboxylic acids used in preparing the hydroxy-functional polyester are used in amounts ranging from about 10 to 30 and preferably in amounts ranging from about 15 to 25 parts by weight. The saturated monocarboxylic acids are characterized by the formula:

wherein R is hydrogen or a branched alkyl or straight chain alkyl or cyclic alkyl of 1 to 6 carbon atoms per molecule including such monocarboxylic acid as formic acid, acetic acid, butyric acid, pivalic acid, propionic acid, valeric acid, caproic acid, and combinations thereof in any proportion. It may be desirable to use a small proportion of a benzoic acid by replacing some of either the unsaturated or saturated monocarboxylic acids. Therefore, up to from about 15 parts by weight and preferably from 8 to 12 parts by weight of a benzoic acid may be used together with the unsaturated monocarboxylic acid and the saturated carboxylic acid in preparing the hydroxy-functional reactive polyester diluents.

The hydroxy-functional polyester diluents prepared in accordance with this invention may be further modified by copolymerization with at least one acrylic monomer and preferably a hydroxy-substituted acrylic monomer. The acrylic monomers are used in amounts ranging from about 0 to 50 and preferably in amounts ranging from 1.0 to 30 parts by weight of at least one acrylic monomer, i.e. a hydroxy-substituted acrylic monomer, with 50 to 100 parts by weight and preferably from about 70 to 90 parts by weight of the hydroxy-functional polyester diluent. The hydroxy-functional polyester diluents of this invention may be modified by co-polymerizing the polyester with at least one acrylic monomer selected from the group consisting of the alkyl methacrylates, alkyl acrylates, acrylic and methacrylic acids, and hydroxyl-containing acrylates, such as hydroxylalkyl acrylate or hydroxyalkyl methacrylate and any combination or mixtures of these vinyl monomers in any proportion. More specifically, the preferred hydroxyalkyl acrylates useful for purposes of this invention, include not only the mono- and polyacrylates such as the mono- or polyhydroxy alkyl di- and triacrlyates or alkyl-acrylates, e.g. the methacrylates and ethacrylates, but also the halogen-substituted acrylates such as the chlorine or bormine-substituted mono- or polyhydroxy alkyl acrylates, e.g. the mono- or polyhydroxy alkyl chloroacrylates or hydroxy-chloroalkyl diacrylates or dialkacrylates. More specifically, the hydroxyalkyl acrylates, for purposes of this invention, may be characterized by the formula:

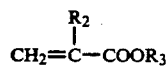

wherein $R_2$ is either hydrogen, a halogen, e.g. chlorine or bromine, an alkyl or substituted alkyl group, e.g. halogen-substituted alkyl group wherein the alkyl group has 1 to 2 carbon atoms and $R_3$ is a mono-or polyhydroxyalkyl or substituted alkyl, e.g. halogen-substituted hydroxyalkyl group having up to 12 and preferably 2 to 8 aliphatic carbon atoms.

In general, the acrylates may be described as esters of acrylic or substituted-acrylic acid including, for example, 2-hydroxypropyl acrylate, 3-hydroxybutyl acrylate, 4-hydroxypentyl acrylate, 5-hydroxypentyl acrylate, 5-hydroxyhexyl acrylate, 2-hydroxybutyl acrylate, 2-hydroxyethyl methacrylate, 2-hydroxyethyl chloroacrylate, 2-hydroxyethyl acrylate, 2-hydroxyethyl ethacrylate, hydroxybutyl ethacrylate, 3-hydroxypropyl methacrylate, 3 hydroxypropyl chloroacrylate, 3-hydroxybutyl acrylate, 4-hydroxybutyl methacrylate, 3-hydroxybutyl ethacrylate, 3-hydroxypropyl ethacrylate, 3-hydroxybutyl chloroacrylate, 3-hydroxypropyl acrylate, 3-hydroxypropyl 2-chloroacrylate, 4-hydroxybutyl acrylate, 3-hydroxyethyl 2-chloroacrylate, 3-hydroxybutyl chloromethacrylate, 5-hydroxypentyl acrylate, 2-hydroxypropyl chloromethacrylate, 5-hydroxypentyl methacrylate, 6-hydroxyhexyl acrylate, 2-hydroxybutyl chloromethacrylate, 2-hydroxyethyl chloroethacrylate, 3-hydroxybutyl methacrylate, 2-hydroxyethyl chloromethacrylate, 2-hydroxypropyl chloroethacrylate, 2-hydroxybutyl dichloroethacrylate, 2-hydroxybutyl chloromethacrylate, 3-hydroxypeopyl-chloromethacrylate, 3-hydroxypropyl chloroethacrylate, 3-hydroxyhexyl chloromethacrylate, 3-hydroxypentyl 2-chloroacrylate, 3-hydroxybutyl bromomethacrylate, 2-hyeroxybutyl chloromethacrylate, 4-hydroxybutyl 2-chloroethacrylate, 3-hydroxypentyl 2-chloroethacrylate, 3-hydroxypropyl 2-bromoethacrylate, 4-hydroxybutyl 2-bromoethacrylate, 5-hydropxyhexyl methacrylate, 6-hydroxypentyl chloromethacrylate and various other vinyl or acrylic esters containing at least one free alcoholic hydroxyl group, e.g. a mono- or polyhydroxy alkyl ester of acrylic, methacrylic or ethacrylic acid.

Other acrylic esters that can be used as the acrylic monomer have at least one free hydroxyl group including polyethylene glycol methacrylate, diethylene glycol methacrylate, triethylene glycol methacrylate, tetraethylene glycol methacryate, dipropylene glycol methacrylate, tetraethylene glycol chloroacrylate, tetraethylene glycol acrylate, tetraethylene glycol dichloroacrylate, glycerol methacrylate, pentaerythritol methacrylate, diethylene glycol monoacrylate, triethylene glycol monoacrylate, dipropylene glycol monoacrylate, trimethylol ethane diacrylate, trimethylol propane diacrylate, pentaerythritol triacrylate, glycerol acrylate, pentaerythritol monoacrylate, trimethylol ethane monoacrylate, trimethylol propane monoacrylate, trimethylol ethane chloroacrylate, trimethylol propane methacrylate, trimethylol butane methacrylate, tetramethylene glycol chloroacrylate, triethylene glycol methacrylate, tetraethylene glycol acrylate, pentaerythritol dichloroacrylate, dipentaerythritol diacrylate, dipentaerythritol triacrylate pentaerythritol dimethacrylate, pentaerythritol methacrylate and combinations of any of these hydroxy-containing acrylates in various proportions.

Styrenes that may be used in combination with the acrylic monomers may be characterized by the formula:

wherein R is hydrogen or an alkyl group of 1 to 4 carbon atoms, e.g. tertiarybutyl styrene and may be present in amounts ranging from about 0% to 70% and preferably in amounts ranging from 5 to 30 parts by weight of the total mixture of acrylic monomers. The alkyl-substituted styrene may be either an ortho-, meta- or para-alkyl-substituted styrene such as para-substituted tertiary-butyl styrene.

The hydroxy-functional polyester reactive diluents or the acrylic-modified hydroxy-functional polyester reactive diluents may be blended with conventional thermosetting or thermoplastic resins normally used in the formulation of coatings. The polyester diluent including the acrylic-modified hydroxy-functional diluents may be blended in amounts ranging from about 1.0 to 75 parts by weight of the polyester diluent with 25 to 99 parts by weight and preferably 50 to 90 parts by weight of the thermosetting or thermoplastic film-forming polymers. These film-forming polymers are well known and include various paint vehicles such as the acrylic lacquers and enamels, nitrocellulose lacquers, alkyd enamels, polyester enamels and polyurethane enamels.

The acrylic film-forming polymers are typically polymers or copolymers of one or more alkyl esters of acrylic acid or methacrylic acid, optionally together with one or more other ethylenically unsaturated monomers. Suitable acrylic esters for either type of polymer include methyl methacrylate, ethyl methacrylate, propyl methacrylate, butyl methacrylate, ethyl acrylate, butyl acrylate, vinyl acetate, acrylonitrile, etc. Where the polymers are required to be of the crosslinking type, suitable functional monomers which can be used in addition to those already mentioned include acrylic or methacrylic acid, hydroxy ethyl acrylate, 2-hydroxy propyl methacrylate, glycidyl acrylate, tertiary butyl amino ethyl methacrylate, etc. If desired, the acrylic polymers can be modified by the incorporation of alkyd polymers as well.

Typically, the acrylics are prepared by conventional free radical addition polymerization techniques. If desired, the polymerization can be catalyzed by conventional catalysts known in the art such as azo, peroxy, or redox catalysts. Typically, the acrylic monomers are heated at temperatures ranging from about 180° F. to 400° F. and especially 200° F. to 300° F. to effect the polymerization. It is normally preferred to prepare the polymers by solution polymerization in inert organic solvents.

Representative acrylic lacquers are described in U.S. Pat. No. 4,168,249 and representative acrylic alkyd enamels are described in U.S. Pat. No. 3,844,993. Representative acrylic enamels are taught in U.S. Pat. No. 4,124,551. The teachings of all these patents are hereby incorporated by reference. Commercially available acrylic lacquers include those sold under various trade designations such as "Pro-Kril" by Acme, a marketing unit of Sherwin-Williams, "Lucite" by the DuPont Co., and "Duracryl" by Ditzler.

Nitrocellulose lacquers are also well known and commercially available nitrocellulose lacquers include those sold under the trade designation "Duco" by DuPont Co.

Thermosetting alkyd or polyester enamels are also well known and can be prepared in a known manner by the condensation of polyhydric alcohols and polycarboxylic acids or anhydrides, with or without the inclusion of natural drying oil fatty acids. The polyesters or alkyds may contain a proportion of free hydroxyl and/or carboxyl groups which are available for reaction, if desired, with suitable crosslinking agents.

Polyurethane vehicles are also well known and can be prepared in a known manner by the reaction of polyhydric alcohols and polyisocyanates. Representative acrylic polyurethane enamels are described in U.S. Pat. No. 3,558,564 and the teaching of which is hereby incorporated by reference.

When these film-forming vehicles are thermosetting vehicles, they will typically also contain a crosslinking agent such as a polyisocyanate, which may be blocked, a polyepoxide, or a nitrogen resin such as a condensate of an aldehyde, typically formaldehyde, with a nitrogenous compound such as urea, melamine or benzoguanamine or a lower alkyl ether of such a condensate. In those cases where the coating composition involves a thermosetting vehicle having functional groups which are reactive with an isocyanate it is usually necessary to add the isocyanate shortly before the application of the coating to minimize the increase of viscosity resulting from the reaction of the isocyanate groups with the reactive groups on the thermosetting vehicle.

The following illustrates the hydroxy-functional and acrylic-modified hydroxy-functional polyester diluents and the method of preparing said polyester diluents in accordance with this invention.

EXAMPLE 1

Hydroxy-Functional Polyester Diluent

A 5-liter reactor equipped with a mechanical stirrer, reflux condenser, thermometer, nitrogen inlet, Dean-Stark water trap and heating mantle was charged with 1,788 parts by weight of trimethylolpropane, 860 parts by weight of crotonic acid, 740 parts by weight of propionic acid and 200 parts by weight of xylene. The reactants were heated to 450° F. and were processed to an acid number of 2 to 3. A hydroxy-functional polyester having a number average molecular weight of 146, as determined by gel permeation chromatography using polystyrene as the standard was obtained.

EXAMPLE 2

Acrylic Modified Hydroxy-Functional Polyester

A 5 liter polymerization reactor equipped with a mechanical stirrer, reflux condenser, thermometer, nitrogen inlet, Dean-Stark water trap, heating mantle and fluid metering pump was charged with 2,398 parts by weight of the hydroxy-functional polyester diluent of Example 1 and heated to 320° F. under nitrogen. A monomer mixture comprised of about 118 parts by weight of styrene, 102 parts by weight of methyl methacrylate, 169 parts by weight of butyl methacrylate, 160 parts by weight of hydroxyethyl methacrylate, 10 parts by weight of methacrylic acid and 25 parts by weight of tertiary butyl perbenzoate was metered into the polymerization reactor at a uniform rate over a period of 3 hours. Additional amounts of tertiary butyl perbenzoate (10 parts by weight) were added over about 30 minutes at 320° F. Heating of the reactants was maintained at reflux for an additional 2 hours. An acrylic-modified hydroxy-functional polyester diluent was obtained having a number average molecular weight of 270, as determined by gel permeation chromatography using polystyrene as the standard.

EXAMPLE 3

Acrylic-Modified Hydroxy-Functional Polyester

A 5-liter polymerization reactor equipped with a mechanical stirrer, reflux condenser, thermometer, nitrogen inlet, Dean-Stark water trap, heating mantle and a fluid meter pump was charged with 701 parts by weight of the hydroxy-functional polyester diluent of Example 1 and heated to 320° F. under nitrogen. A monomer mixture comprising 59.5 parts by weight of styrene, 56.3 parts by weight of methyl methacrylate, 85.1 parts by weight of butyl methacrylate, 80.5 parts by weight of hydroxyethyl methacrylate, and 17.6 parts by weight of tertiary butyl perbenzoate were metered into the polymerization reactor at a uniform rate over a 3 hour period. Additional amounts of the tertiary butyl perbenzoate (10 parts by weight) scavenger catalyst were added over 30 minutes at 320° F. Heating was maintained at reflux for an additional 2 hour period. An acrylic-modified hydroxy-functional polyester diluent was obtained and characterized as having a number average molecular weight of about 200, as determined by gel permeation chromatography using polystyrene as the standard. These hydroxy-functional polyester diluents, including the acrylic-modified hydroxy-functional polyester diluent, (Examples 1, 2, and 3) were blended with film-forming polymers, i.e. hydroxy-functional acrylates containing isocyanates, in the ratio of 30 parts by weight of the hydroxy-functional polyester diluents with 70 parts by weight of the hydroxy-functional acrylic containing the isocyanate as illustrated in the data of Tables 1, 2 and 3.

EXAMPLE 4

A 5-liter reactor equipped with a mechanical stirrer, reflux condenser, thermometer, nitrogen inlet, Dean-Stark water trap and heating mantle was charged with 492.2 parts by weight trimethylol propane, 225.3 parts by weight crotonic acid, 193.8 parts by weight propionic acid, 88.7 parts by weight para-t-butyl benzoic acid and 50 parts xylene as reflex solvent. This is then heated to 450° F. and approximately 103 grams of water is removed. The vehicle is processed to an acid number 2 to 3. A hydroxy-functional polyester, having a number average molecular weight of 160 as determined by gel permeation chromatography using polystyrene as standard, was obtained. Theoretical number average molecular weight was 242 and hydroxyl number was 329.

The formulation of the hydroxy-functional polyester and acrylic-modified hydroxy-functional polyester diluents with conventional thermosetting and thermoplastic film-forming resins are illustrated in the following Tables:

TABLE I

RESIN COMPOSITION AND CHARACTERISTICS

| | Percent By Weight | | |
|---|---|---|---|
| | Example 1 | Example 2 | Example 3 |
| Reactants | | | |
| Trimethylolpropane | 52.77 | — | — |
| Crotonic Acid | 25.38 | — | — |
| Propionic Acid | 21.85 | — | — |
| Example 1 | — | 80.14 | 70.10 |
| Styrene | — | 3.94 | 5.95 |
| Methyl Methacrylate | — | 3.41 | 5.63 |
| Butyl Acrylate | — | 5.65 | 8.51 |
| Hydroxyethyl Methacrylate | — | 5.34 | 8.05 |
| Methacrylic Acid | — | 0.35 | — |
| t-butyl perbenzoate | — | 1.17 | 1.76 |
| Solvent | Xylene | Xylene | Xylene |
| Characteristics | | | |
| % NVM (Theo.) | 98.0 | 98.0 | 98.0 |
| Viscosity | G | 13–16 | 40+ |
| AV | 2.3 | 5.9 | 4.2 |
| Color (G&H) | 2 | 1–2 | 1–2 |
| Clarity | CLR | CLR | CLR |
| OH. Eq. Wt. (solid resin) | 171 | 200 | 211 |
| $M_w$ | 177 | 1,600 | 1,000 |
| $M_n$ | 146 | 270 | 200 |
| $P_d$ | 1.2 | 5.9 | 4.6 |

TABLE I-continued

RESIN COMPOSITION AND CHARACTERISTICS

| | Percent By Weight | | |
|---|---|---|---|
| | Example 1 | Example 2 | Example 3 |
| Hydroxyl Number* | 305 | 256 | 221 |

*Measured.

TABLE II

VISCOSITY STUDY AND POT LIFE OF LOW VOC COATINGS
(Blend of Polyester Diluents with Film-Forming Acrylic and Isocyanate)

| Polyester Diluents | Example 1 | Example 2 | Example 3 |
|---|---|---|---|
| Init. Visc.* | 23" | 26" | 29" |
| 1 Hr. | 25" | 29" | 29" |
| 2.5 Hrs. | 29" | 36" | 35" |
| 3.5 Hrs. | 32" | 38" | 42" |
| 4.5 Hrs. | 35" | 43" | 45" |
| 5.5 Hrs. | 41" | 49" | 51" |
| VOC | 3.43 | 3.43 | 3.43 |
| % NVM | 59.15 | 59.29 | 59.32 |
| Eq. Wt. | 117 | 138 | 151 |
| NCO/OH Ratio | .70/1.0 | .78/1.0 | .84/1.0 |
| Clear Blend with Hydroxy-Functional Acrylic Polymer (70/30) | | | |
| Init. Visc. | 18" | 16" | 15" |
| VOC | 3.13 | 3.12 | 3.10 |
| % NVM | 62.00 | 62.04 | 61.97 |

*Viscosity increase with time - #2 Zahn cup (hydroxy-functional acrylic polymer with isocyanate)

TABLE III

FILM PROPERTIES WITH FILM-FORMING POLYMERS**

| Polyester Diluents* | Example 1 | Example 2 | Example 3 |
|---|---|---|---|
| Air Dry | | | |
| Tape Test | | | |
| 8 Hrs. | Tacky | Tacky | Tacky |
| 24 Hrs. | Pass | Pass | Pass |
| Appearance | No Haze | No Haze | No Haze |
| Pendulum Hardness (24 Hrs.) | 9 | 24 | 33 |
| Gloss 20°/60° | 72.2/87.3 | 81.0/87.2 | 80.3/87.1 |
| Solvent (MEK) 24 Hrs. | Pass | Pass | Pass |
| Force Dry - 180° F./30 min. | | | |
| Tape Test - 8 Hrs. | Fail | Pass | Pass |
| Appearance | No Haze | No Haze | No Haze |
| Pendulum Hardness (24 Hrs.) | 7 | 20 | 80 |
| Gloss 20°/60° | 82.4/87.7 | 81.1/88.5 | 83.9/89.4 |
| Solvent (MEK) 24 Hrs. | Pass | Pass | Pass |

*30% blend of polyester diluent in 70% of acrylic film-forming polymers.
**Acrylic polymer containing isocyanate crosslinking agent.

TABLE IV

POLYESTER DILUENT COMPOSITIONS AND CHARACTERISTICS

| Components | Control* | Example 5 | Example 6 | Example 7 |
|---|---|---|---|---|
| Trimethyol Propane | 52.77 | 49.23 | 59.24 | 52.77 |
| Crotonic Acid | 25.38 | 22.53 | 28.49 | 25.38 |
| Propionic Acid | 21.85 | 19.38 | 12.27 | 21.85 |
| p-t-butyl Benzoic Acid | | 8.86 | — | — |
| NVM (Theo.) | 98% | 98% | 98% | 98% |
| Viscosity | G-H | F-G | M-N | F-G |
| Aci Value | 2.5 | 3.9 | 2.7 | 3.2 |
| Color | 2 | 2 | 2 | 2 |
| Clarity | Clear | Clear | Clear | Clear |
| OH Eq. Wt. (Solid Resin) | 152 | 144 | 110 | 171 |
| Hydroxyl Number (Theo.) | 368 | 329 | 507 | 368 |
| $M_n$ (Theo.) | 227 | 242 | 206 | 226 |

*Control is Example 1 with 2% by weight of xylene.

TABLE V
PERFFORMANCE PROPERTIES OF LOW VOC SYSTEMS (TOPCOAT)

| | Control | Example 5 | Example 6 |
|---|---|---|---|
| Clear (Uncatalyzed) | | | |
| Initial Visc. #2 Zahn Cup | 18" | 14" | 15" |
| VOC | 3.13 | 3.07 | 3.09 |
| NVM | 62% | 62.1% | 62.1% |
| Black Acrylic Polymer with Isocyanate | | | |
| Initial Viscosity | 23" | 27" | 29" |
| 1 Hr. | — | — | — |
| 2 Hrs. | 29" | 35" | 40" |
| (Air Dry) | | | |
| Hand Slick (4.5 Hrs.) | Pass | Pass | Pass |
| Wt/Gal. | 8.40 | 8.10 | 8.15 |
| NCO/OH | — | 1.2/1 | 1.2/1 |
| Tape Test (16 Hrs.) | Pass | Pass | Pass |
| DFT | — | 2.6 | 2.0 |
| Appearance | No Haze | No Pop Sl. Peel | Pop Sl. Peel |
| Pend. Hardn. (40 Hrs.) | 9- | 40 | 62 |
| Gloss | | | |
| 20° | 72.2 | 83.5 | 85.4 |
| 60° | 87.3 | 91.0 | 91.6 |
| Solvent (MEK) 24 Hrs. | Pass | Pass | Pass |
| DIO | — | 87.4 | 77.9 |
| Across Grain DOI | — | 90.8 | 83.8 |
| (Force Dry) - 30 Min. @ 180° F. | | | |
| Tape Test | Fail | Pass | Pass |
| DFT | — | 1.85 | 2.31 |
| Appearance | No Haze | No Pop Sl. Peel | Pop Sl. Peel |
| Pend. Hard. (24 Hrs.) | 7 | 24 | 47 |
| Gloss | | | |
| 20° | 82.4 | 82.7 | 81.1 |
| 60° | 87.7 | 90.2 | 90.8 |
| DOI | — | 74.9 | 70.0 |
| Across Grain DOI | — | 87.4 | 84.0 |
| Solvent (MEK) | Pass | Pass | Pass |

TABLE VI

| Components | (paint formula) Parts By Weight |
|---|---|
| Polyester Diluent of Example 1 with Acrylic Film-Forming Polymer (30/70) | 10 to 90 |
| Organic Solvent | 0 to 30 |
| Pigment (i.e. TiO2) | 10 to 40 |
| Fillers (e.g. Carbonates) | 0 to 30 |
| Extenders | 0 to 30 |
| Driers | 0.01 to 10 |
| Catalyst (e.g. Cobalt Salts) | 0.01 to 1.0 |
| Defoamers (e.g. Silicones) | 0.01 to 2.0 |

Typically, the coating composition will include other additives to adjust the performance and application characteristics of the coating. Normally, the coating composition will include an inert organic solvent typically ranging from 1.0 to 30% by weight based upon the total weight of the coating. Useful inert solvents for the coating composition include aromatic hydrocarbons such as toluene, xylene, ethyl benzene, aromatic naphtha, etc.; aliphatic hydrocarbons such a mineral spirits, hexane, aliphatic naphtha, etc.; esters such a butyl acetate, ethylene glycol monoethyl ether acetate, ethylene glycol monobutyl ether acetate, etc.; and ketones such as ethyl amyl ketone, etc.

The coating may also contain other additives such as flow agents, catalysts, ultra violet light absorbers, etc. The coating may be applied to any substrate, such as metal, plastic, wood, glass, synthetic fibers, etc. by brushing, dipping, roll coating, flow coating, spraying or other method conventionally employed in the coating industry. If desired, the substrate may be primed prior to the application of the coating.

Typical pigments used in the coating compositions include the various metal oxides, such as titanium dioxide, zinc oxide, iron oxide, and metal flakes, such as aluminum or bronze flakes, metal powders, and the molybdate pigments, such as molybdate, orange pigments, sulfate pigments, carbonate pigments, carbon black, silica pigments and various other organic or inorganic pigments commonly used in the preparation of coatings. Pigments are generally based on the weight of the binder or vehicle in a ratio of about 0.5-100 to 200-1 where the binder or vehicle is the film forming constituent of the coating. In formulating paints, it is a practice in addition to including the primary pigments, such as $TiO_2$, to use other materials such as fillers or extenders, e.g. the carbonates, talcs, silicates, clays, micas, and the like in combination with the primary pigment. The relative proportion of the primary pigment and the fillers or extenders is not critical and may be varied over a wide range. Generally, however, the primary pigments are present at a pigment volume concentration to provide the desired paint covering or hiding, whereas the extender pigment is present in amounts to provide the paint with the total required pigment volume concentration.

While this invention has been described with respect to a number of specific embodiments, it is obvious that there are other variations and modifications which can be made without departing from the spirit and scope of the intention as more particularly set forth in the appended claims.

The invention claimed is:

1. A hydroxy-functional polyester diluent having a number average molecular weight less than about 500 characterized as having an average of at least one hydroxyl group per molecule and an average of at least one polymerizable double bond per molecule derived from the reaction of:
   (a) at least one triol having a molecular weight less than about 200,
   (b) at least one low molecular weight unsaturated monocarboxylic acid having the formula:

$$R_2-C=C-COOH$$
$$\quad\quad\;\;|$$
$$\quad\quad\;\;R_1$$

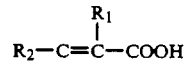

wherein $R_1$ is either hydrogen or an alkyl group of 1 to 3 carbon atoms and $R_2$ is an aliphatic group of 1 to 4 carbon atoms or an aryl group, and
   (c) at least one low molecular weight saturated monocarboxylic acid having the formula:

$$R-COOH$$

wherein R is hydrogen or a branched alkyl or straight chain alkyl or cyclic alkyl of 1 to 6 carbon atoms;
   said triol being present in a stoichiometric amount to provide excess hydroxyl groups and said unsaturated monocarboxylic acid being present in amounts sufficient to provide at least one ethylenically unsaturated group for each molecule of triol.

2. The hydroxy-functional polyester diluent of claim 1 further characterized in that the triol is trimethylolpropane, the unsaturated monocarboxylic acid is crotonic acid and the saturated monocarboxylic acid is propionic acid.

* * * * *